United States Patent [19]
Dodge

[11] Patent Number: 5,518,010
[45] Date of Patent: May 21, 1996

[54] RESTRAINT DEVICE

[76] Inventor: James L. Dodge, 375 "A" Owosso Dr., Eugene, Oreg. 97404

[21] Appl. No.: 419,244

[22] Filed: Apr. 10, 1995

[51] Int. Cl.⁶ .............................. A61B 19/00; A61F 5/37
[52] U.S. Cl. ........................ 128/869; 128/876; 128/878
[58] Field of Search .................... 128/869–876, 128/877, 878, 879; 70/15, 16, 17; 119/760

[56] References Cited

U.S. PATENT DOCUMENTS

| | | | |
|---|---|---|---|
| 1,410,802 | 3/1922 | Foster . | |
| 3,621,681 | 11/1971 | Mikesic | 70/16 |
| 4,321,890 | 3/1982 | Lange | 128/869 |
| 4,949,679 | 8/1990 | Wolfer | 128/878 |
| 5,038,799 | 8/1991 | Fowler | 128/878 |
| 5,092,592 | 3/1992 | FitzMaurice | 70/16 |
| 5,398,383 | 3/1995 | Bingold | 70/16 |

*Primary Examiner*—Michael A. Brown
*Attorney, Agent, or Firm*—James D. Givnan, Jr.

[57] ABSTRACT

A bar is provided with curved end segments in which the raised upper arms of a person are confined. Straps mounted on the bar have free ends which are attachable to the curved end segments to restrain the upper arms in place on the bar. Fabric closure members secure the strap ends in place. A curved appendage on the bar seats against the back of the person's neck. An apertured anchor plate on the bar receives handcuffs or plastic ties for securing the person's overlapped wrists in an area rearward of the neck.

8 Claims, 1 Drawing Sheet

U.S. Patent  May 21, 1996  5,518,010
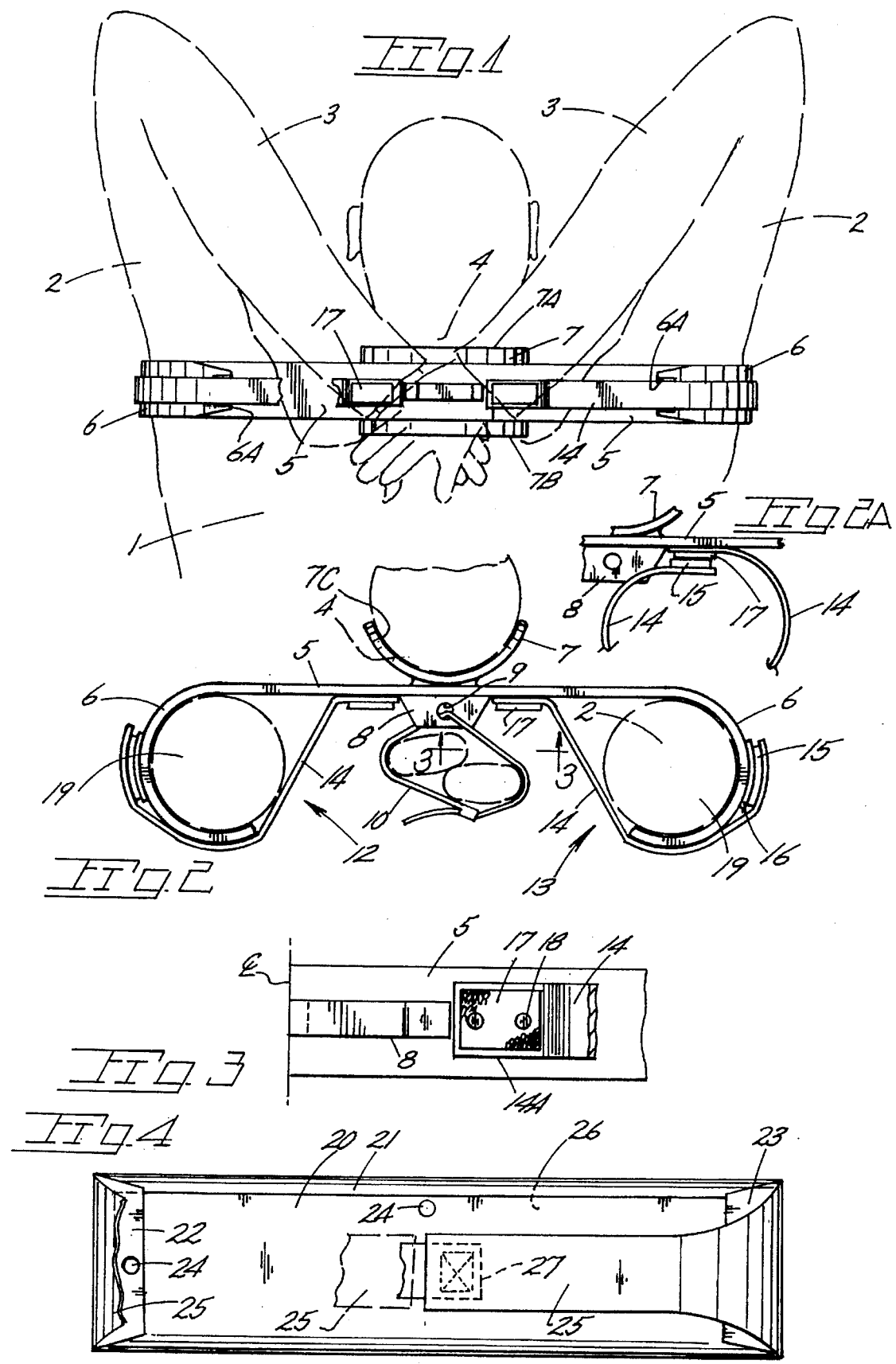

RESTRAINT DEVICE

BACKGROUND OF THE INVENTION

The present invention pertains generally to restraint devices and particularly such a device for placement on the human body to restrain arm movement. Typically persons arrested are subjected to being handcuffed or otherwise having their wrists joined by a lockable tie.

Known devices for coupling of a person's hands or wrists have a drawback in that the person is not physically prevented from running. Further, handcuffing or joining of the wrists by means of a plastic tie fail to prevent use of the joined hands, particularly when the wrists are secured in front of the individual.

A problem also exists in the handcuffing or otherwise joining a prisoner's hands in that transport in a vehicle entails some difficulty in the use of automotive restraint belts and harnesses. Additionally, damage to seating areas of a patrol car may result in the handcuffed person intentionally damaging the seating area with the handcuffs or forcefully displace or move their joined arms to inflict injury as well as damage to equipment.

U.S. Pat. No. 1,410,802 discloses a pair of handcuffs oppositely spaced from a lockable ring for placement on the neck of a prisoner.

SUMMARY OF THE INVENTION

The present invention is embodied within a restraint for installation on the upper arms when raised to the near vertical with the lower arms extending downwardly and secured to the present device.

The present restraint includes a main member of bar configuration having reversed end segments which, when in place on the upper arms, virtually secure same against movement. Strap means provide closures for the reversed end segments to ensure upper arm confinement therein in instances where the size of the individual permits limited upper arm movement. A collar-like appendage in place on the bar for neck engagement restricts lateral movement of the bar. Additionally, the collar arrangement engages the back of the individual's head and the shoulder area to confine the present restraint against vertical displacement relative the torso. An apertured plate or flange member receives handcuffs or a nylon tie the latter of the type having lock for the tie. Accordingly, a restrained individual with the present restraint in place has both arms immobilized in a raised, radically bent position with the wrist area of each arm being snugly attached to the restraint to locate the wrists proximate to and rearward of the neck. Straps are provided with closure members which cooperate with additional closure members in place on the curved end segments to close the arm occupied end segments.

Important objectives of the present invention include the provision of a restraint which immobilizes the person's arms with the wrists being positioned and immobilized rearward of the person's neck; the provision of a restraint having a collar-like member which fits about a portion of the person's neck to prevent lateral and vertical movement of the restraint relative the body; the provision of a restraint which serves to position the upper arms in a near vertical position while the lower arms are flexed to locate the wrists thereof immediately rearward of the neck for coupling to the bar by a lockable device such as handcuffs or ties; the provision of a restraint for use by law enforcement personnel which is of light weight construction to avoid being used as a weapon by the person apprehended while permitting convenient transport by the user and convenient placement on the person being apprehended; the provision of a restraint to locate the arms in a raised, fully flexed position with the wrists secured in place rearward of the neck to discourage running by the person apprehended.

BRIEF DESCRIPTION OF THE DRAWINGS

FIG. 1 is a front elevational view of the restraint in place with a person shown in phantom lines;

FIG. 2 is a top plan view of FIG. 1;

FIG. 2A is a fragmentary top plan view of the restraint with a strap shown in a stowed position;

FIG. 3 is a fragmentary front elevational view taken along line 3—3 of FIG. 2; and FIG. 4 is a plan view of a carrying case for the present device including a shoulder strap to facilitate convenient carrying of the restraint in a snug manner on the body of a user.

DETAILED DESCRIPTION OF THE PREFERRED EMBODIMENTS

With continuing attention to the drawings, the reference numeral 1 indicates the back of the upper torso of a person with the person's upper arms indicated at 2 and the lower arms at 3. The posterior of the person's neck is indicated at 4.

With attention now to the present restraint, a bar at 5 terminates at its ends in curved reversed end segments 6 each of which preferably describes an arc preferably somewhat greater than a semi-circle. In place on the mid-portion of the bar is an appendage 7 with a recessed surface 7C (FIG. 2) to rest against the posterior neck surface 4 and having upper and lower edges 7A and 7B (FIG. 1) which are confined against vertical displacement by areas of the person's head and shoulders.

A plate or flange 8 projects from the central area of bar 5 on the same side of the bar as curved end segments 6 while the plate appertured at 9 to receive anchoring means for securing a pair of handcuffs or a tie 10 or multiple ties if each hand is to be separately restrained.

Indicated generally at 12 and 13 are strap means with straps at 14 suitably attached at one of their ends 14A in permanent fashion to bar 5. Each strap is of a length to pass over the distal end 6A of an end segment 6 and at least partially thereabout. A fabric closure member 15 on the free end of each strap 14 engages a cooperating closure member 16 in place on an end segment 6 of the bar to close the area at 19 defined by the end segment and restrain an upper arm in place therein regardless of physical differences in the persons being restrained. Any inward lateral movement of either upper arm 2 is prevented by strap 14 when operatively in place as shown in FIG. 2. FIG. 2A shows a strap 14 in a stowed position whereat a fabric closure member at 17, in place on the fixedly mounted end of the strap, receives the earlier noted fabric closure member 15 on the free end of the strap. Straps 14 may be fastened to bar 5 by rivets at 18.

The curved end segments 6 preferably define arcuately extending relieved areas at 6A which contribute to prevented vertical displacement of a strap 14 or channels off the end segment.

In FIG. 4 a carrying device for the present restraint is shown which may be worn by the user in the manner of a bandolier to avoid interference with other equipment or accessories on the user. The carrying device is of pliable material folded over the restraint device with the folded sides 20–21 and ends 22–23 of the device being held in place by snaps 24 permitting one handed access to the restraint device therein when the carrying device is on the user's body. A strap 25 is integral with a back 26 of the carrying device. An elastic insert at 27 also facilitates snug placement on the user's body.

While I have shown but one embodiment of the invention, it will be apparent to those skilled in the art that the invention may be embodied still otherwise without departing from the spirit and scope of the invention.

Having thus described the invention, what is desired to be secured by a Letters Patent is:

1. A restraint device attachable to the upper arms of a person and comprising, a bar terminating at its ends in reversed end segments each defining an open area to receive an upper arm, an appendage with a recessed surface centrally disposed on said bar for engagement with the person's neck, and anchoring means defining an opening for the passage therethrough of a lockable restraint for passage about the wrists of the person.

2. The restraint device claimed in claim 1 additionally including strap means carried by said bar and attachable to each of said reversed end segments to close said reversed end segments.

3. The device claimed in claim 2 wherein said reversed end segments and said strap means include cooperating fabric closure members.

4. The device claimed in claim 3 wherein said bar carries fixedly mounted fabric closure members for retention of a strap means in a stowed nonoperational position.

5. A restraint device for confining limbs of a person and including, a bar terminating in reversed end segments to define open areas each for the reception of a limb, an appendage on the bar for placement at least partially about another body member, and anchoring means on said bar including an opening through which a lockable restraint may be inserted subsequent to passage about a limb.

6. The restraint device claimed in claim 5 additionally including straps carried by said bar and attachable to said reversed end segments.

7. The device claimed in claim 6 wherein said reversed end segments and said straps carry cooperating fabric closure members.

8. The device claimed in claim 7 additionally including fixedly mounted fabric closure members for retention of said straps in a stowed position, fasteners securing said fixedly mounted fabric closure members to said bar.

\* \* \* \* \*